United States Patent
Perraut et al.

(10) Patent No.: US 10,918,337 B2
(45) Date of Patent: Feb. 16, 2021

(54) VEHICLE SEAT WITH INTEGRATED SENSORS

(71) Applicant: Faurecia Automotive Seating, LLC, Auburn Hills, MI (US)

(72) Inventors: John M. Perraut, Rochester Hill, MI (US); Christopher Kus, Auburn Hills, MI (US)

(73) Assignee: Faurecia Automotive Seating, LLC, Auburn Hills, MI (US)

( * ) Notice: Subject to any disclaimer, the term of this patent is extended or adjusted under 35 U.S.C. 154(b) by 407 days.

(21) Appl. No.: 15/613,578

(22) Filed: Jun. 5, 2017

(65) Prior Publication Data
US 2017/0347961 A1    Dec. 7, 2017

Related U.S. Application Data

(60) Provisional application No. 62/345,253, filed on Jun. 3, 2016.

(51) Int. Cl.
*A61B 5/00* (2006.01)
*A61B 5/08* (2006.01)
(Continued)

(52) U.S. Cl.
CPC ........ *A61B 5/6893* (2013.01); *A61B 5/02405* (2013.01); *A61B 5/0816* (2013.01);
(Continued)

(58) Field of Classification Search
None
See application file for complete search history.

(56) References Cited

U.S. PATENT DOCUMENTS 3,580,245 A    5/1971    Dill
4,031,579 A    6/1977    Larned
(Continued)

FOREIGN PATENT DOCUMENTS

CN    1572575        2/2005
CN    1956680 A      5/2007
(Continued)

OTHER PUBLICATIONS

N. Mizuno and K. Washino, "A model based filtering technique for driver's heart rate monitoring using seat-embedded vibration sensors," 2014 6th International Symposium on Communications, Control and Signal Processing (ISCCSP), Athens, 2014, pp. 137-140, doi: 10.1109/ISCCSP.2014.6877834. (Year: 2014).*

(Continued)

*Primary Examiner* — Aniss Chad
*Assistant Examiner* — Kelly D Williams
(74) *Attorney, Agent, or Firm* — Barnes & Thornburg LLP

(57) ABSTRACT

An occupant support includes a vehicle seat, a sensor coupled to the vehicle seat, and a controller coupled to the sensor. The sensor provides a signal to the controller and the controller processes and responds to the sensed signal. In illustrative embodiments, a controller includes a sensor module, a filter module, and a biometrics module. The sensor module retrieves sensor data indicative of an occupant of a vehicle seat from one or more sensors of a vehicle. The filter module determines a filter function in a frequency range in which useful biological data may be derived. The filter function identifies one or more frequencies of noise in the sensor data and applies the filter function to the sensor data to generate filtered sensor data. The biometrics module determines biometric data associated with the occupant based on the filtered sensor data.

16 Claims, 4 Drawing Sheets

(51) Int. Cl.
  *A61B 5/11* (2006.01)
  *A61B 5/024* (2006.01)
  *B60N 2/00* (2006.01)

(52) U.S. Cl.
  CPC ............ *A61B 5/1102* (2013.01); *A61B 5/725* (2013.01); *A61B 5/7278* (2013.01); *B60N 2/002* (2013.01)

(56) References Cited

U.S. PATENT DOCUMENTS

| | | | |
|---|---|---|---|
| 4,655,505 | A | 4/1987 | Kashiwamura |
| 4,707,027 | A | 11/1987 | Horvath |
| 4,840,425 | A | 6/1989 | Noble |
| 4,928,090 | A | 5/1990 | Yoshimi |
| 5,069,214 | A | 12/1991 | Samaras |
| 5,155,685 | A | 10/1992 | Kishi |
| 5,462,515 | A | 10/1995 | Tseng |
| 6,055,473 | A | 4/2000 | Zwolinski |
| 6,087,942 | A | 7/2000 | Sleichter, III |
| 6,120,468 | A | 9/2000 | Tseng |
| 6,212,719 | B1 | 4/2001 | Thomas |
| 6,273,810 | B1 | 8/2001 | Rhodes, Jr. |
| 6,422,087 | B1 | 7/2002 | Potter |
| 7,206,631 | B2 | 4/2007 | Kawachi |
| 7,239,945 | B2 | 7/2007 | Hiemer |
| 7,322,652 | B1 | 1/2008 | Tache |
| 7,774,052 | B2 | 8/2010 | Burton |
| 7,862,113 | B2 | 1/2011 | Knoll |
| 8,123,290 | B1 | 2/2012 | Aiken |
| 8,181,292 | B1 | 5/2012 | Pellettiere |
| 8,328,279 | B2 | 12/2012 | Brncick |
| 8,430,817 | B1 | 4/2013 | Al-Ali |
| 8,616,654 | B2 | 12/2013 | Zenk |
| 8,672,411 | B2 | 3/2014 | Gomes |
| 8,725,311 | B1* | 5/2014 | Breed .................. A61B 5/163 701/1 |
| 8,757,726 | B2 | 6/2014 | Oota |
| 8,919,874 | B2 | 12/2014 | Ota |
| 9,135,803 | B1 | 9/2015 | Fields |
| 9,440,657 | B1 | 9/2016 | Fields |
| 9,475,389 | B1 | 10/2016 | Fung |
| 9,505,402 | B2 | 11/2016 | Fung |
| 9,717,345 | B1 | 8/2017 | Caruso |
| 9,848,814 | B2 | 12/2017 | Benson |
| 10,235,859 | B1 | 3/2019 | Hiles |
| 10,258,535 | B2 | 4/2019 | Lem |
| 10,471,864 | B1 | 11/2019 | Tait |
| 2002/0091473 | A1 | 7/2002 | Gardner |
| 2004/0243368 | A1 | 12/2004 | Hiemer |
| 2005/0027416 | A1* | 2/2005 | Basir .................. A61B 5/1102 701/36 |
| 2005/0124864 | A1 | 6/2005 | Mack |
| 2005/0248184 | A1 | 11/2005 | Piffaretti |
| 2006/0025698 | A1 | 2/2006 | Nakagawa |
| 2006/0068693 | A1 | 3/2006 | Kono |
| 2006/0175877 | A1 | 8/2006 | Alionte |
| 2007/0029862 | A1 | 2/2007 | Bargheer |
| 2007/0251749 | A1* | 11/2007 | Breed .................. B60J 10/00 180/273 |
| 2008/0296946 | A1 | 12/2008 | Reynolds |
| 2009/0030576 | A1 | 1/2009 | Periot |
| 2009/0164241 | A1 | 6/2009 | Racioppo |
| 2010/0185068 | A1 | 7/2010 | Park |
| 2010/0229181 | A1 | 9/2010 | Ahuja |
| 2011/0015468 | A1 | 1/2011 | Aarts |
| 2011/0066292 | A1* | 3/2011 | Moriya .................. F16F 15/002 700/280 |
| 2011/0133755 | A1* | 6/2011 | Griffin .................. B60N 2/002 324/633 |
| 2011/0156453 | A1 | 6/2011 | Matsushima |
| 2011/0186560 | A1 | 8/2011 | Kennedy |
| 2011/0304465 | A1 | 12/2011 | Boult |
| 2012/0078123 | A1 | 3/2012 | Futatsuyama |
| 2012/0212353 | A1 | 8/2012 | Fung |
| 2013/0070043 | A1 | 3/2013 | Geva |
| 2014/0031703 | A1 | 1/2014 | Rayner |
| 2014/0039330 | A1 | 2/2014 | Seo |
| 2014/0228649 | A1 | 8/2014 | Rayner |
| 2014/0240132 | A1 | 8/2014 | Bychkov |
| 2014/0276112 | A1 | 9/2014 | Fung |
| 2015/0008710 | A1 | 1/2015 | Young |
| 2015/0051526 | A1 | 2/2015 | Wang |
| 2015/0151658 | A1 | 6/2015 | Burris |
| 2015/0231991 | A1 | 8/2015 | Yetukuri |
| 2015/0239321 | A1 | 8/2015 | Müller |
| 2015/0313475 | A1 | 11/2015 | Benson |
| 2016/0001781 | A1 | 1/2016 | Fung |
| 2016/0019813 | A1 | 1/2016 | Mullen |
| 2016/0029940 | A1 | 2/2016 | Iizuka |
| 2016/0086500 | A1 | 3/2016 | Kaleal, III |
| 2016/0339801 | A1 | 11/2016 | Pereny |
| 2016/0339802 | A1 | 11/2016 | Hanlon |
| 2017/0136842 | A1 | 5/2017 | Anderson |
| 2017/0136922 | A1 | 5/2017 | Von Ballmoos |
| 2017/0158202 | A1 | 6/2017 | Yang |
| 2017/0282930 | A1 | 10/2017 | Kochhar |
| 2017/0285641 | A1 | 10/2017 | Goldman-Shenhar |
| 2017/0312534 | A1 | 11/2017 | Cao |
| 2017/0326013 | A1 | 11/2017 | Hyde |
| 2017/0340214 | A1 | 11/2017 | Benson |
| 2018/0037236 | A1 | 2/2018 | Yamaguchi |
| 2018/0178808 | A1 | 6/2018 | Zhao |
| 2018/0229674 | A1 | 8/2018 | Heinrich |

FOREIGN PATENT DOCUMENTS

| | | |
|---|---|---|
| CN | 103565429 A | 2/2014 |
| CN | 104837403 A | 8/2015 |
| CN | 0104875744 | 9/2015 |
| DE | 102005038289 | 3/2007 |
| DE | 102007053119 | 5/2009 |
| DE | 102009021532 | 11/2010 |
| EP | 1447070 A | 8/2004 |
| JP | 2010264092 | 11/2010 |
| KR | 1020010061858 | 7/2001 |
| KR | 1020140027641 | 3/2014 |
| KR | 0101642697 | 8/2016 |
| WO | 2013109154 | 7/2013 |
| WO | 2013109154 A1 | 7/2013 |
| WO | 02014147828 | 9/2014 |
| WO | 2014147828 | 9/2014 |
| WO | 2015127193 | 8/2015 |
| WO | 2015200224 | 12/2015 |
| WO | 2016070981 | 5/2016 |

OTHER PUBLICATIONS

Chinese Office Action for Chinese Pat. App. No. 201580011844.9 dated Mar. 14, 2019, 3619 CN ||, 12 pages, (brief summary included in English).

Chinese Office Action for Chinese Pat. App. No. 201580011844.9 dated Jul. 12, 2019, 3619 CN ||, 13 pages, (brief summary included in English).

Chinese Office Action for Chinese App. No. 201380064313.2 dated Sep. 28, 2017, 3376 CN ||, 19 pages.

Chinese Office Action for Chinese App. No. 201380064313.2 dated Apr. 12, 2017, 3376 ||, 21 pages.

PCT International Search Report and Written Opinion completed by the ISA/US dated Apr. 22, 2014 and issued in connection with PCT/US2013/071620.

PCT Search Report and Written Opinion completed by the ISA/EP dated May 21, 2015 and issued in connection with PCT/US2015/016803, 13 pages.

Office Action dated May 1, 2019 for U.S. Appl. No. 15/692,396, 4112 US-U || (pp. 1-27).

Office Action dated May 16, 2019 for U.S. Appl. No. 15/626,525, 4081 US-U || (pp. 1-12).

Chinese Rejection Decision for Chinese App. No. 201380064313.2 dated May 17, 2018, 3376 CN ||, 13 pages.

(56) References Cited

OTHER PUBLICATIONS

Office Action dated Nov. 29, 2017 for U.S. Appl. No. 15/235,882; II (pp. 1-7).
Chinese Office Action for Chinese Pat. App. No. 201580011844.9 dated Aug. 28, 2018, 3619 CN II, 19 pages, (brief summary included in English).
European Examination Report for European App. No. 15 707 235.6 dated Feb. 6, 2018, 3619 EP II, 7 pages.
Chinese Office Action for Chinese App. No. 201710799929.9 dated Sep. 27, 2019, 4112 CN II, 14 pages.
Office Action dated Oct. 29, 2019 for U.S. Appl. No. 15/692,396, 4112 US-U II (pp. 1-37).
Office Action dated Mar. 4, 2020 fo U.S. Appl. No. 15/678,710, 3376 US-U II, (pp. 1-14).
Chinese Office Action for Chinese Pat. App. No. 201580011844.9 dated Nov. 19, 2019, 3619 CN II, 13 pages, (brief summary included in English).
Fifth Chinese Office Action for Chinese Pat. App. No. 201580011844.9 dated Mar. 13, 2020, 3619 CN II, 13 pages, (brief summary included in English).
Choi et al., "Noninvaisive cuffless blood pressure estimation usingpulse transit time and Hilbert-Huang transform," Computers and Electridal Engineering Journal, 39, 103-111 (Nov. 8, 2012), 9 pages.
Wong et al., "The Effects of Exercises on teh Relationship between Pulse Transit Time and Arterial Blood Pressure," Proceedings of the 2005 IEEE Enginering in Medicine and Biology 27th Annual Conference, Shanghai, China , Sep. 1-4, 2005, 3 pages.
Office Action dated Apr. 27, 2020 for U.S. Appl. No. 15/626,525, 4081 US-U II (pp. 1-11).
Office Action dated Apr. 30, 2020 for U.S. Appl. No. 15/873,034, 4296 US-U II (pp. 1-24).
European Examination Report for European App. No. 15 707 235.6 dated Apr. 15, 2020, 3619 EP II, 5 pages.
Office Action dated Apr. 30, 2020 for U.S. Appl. No. 15/863,129, 4296 US-U II (pp. 1-23).
Second Chinese Office Action for Chinese App. No. 201710799929.9 dated Jul. 1, 2020, 4112 CN II, 6 pages.
Office Action dated Sep. 3, 2020 for U.S. Appl. No. 15/863,129, 4296 US-U II (pp. 1-15).
Office Action dated Sep. 3, 2020 for U.S. Appl. No. 15/873,034, 4296 US-CON1 II (pp. 1-17).

\* cited by examiner

VEHICLE SEAT WITH INTEGRATED SENSORS

CROSS-REFERENCE TO RELATED APPLICATION

This application claims priority under 35 U.S.C. § 119(e) to U.S. Provisional Patent Application Ser. No. 62/345,253, filed Jun. 3, 2016, which is expressly incorporated by reference herein.

BACKGROUND

The present disclosure relates to a vehicle seat, and particularly to a vehicle seat including a sensor. More particularly, the present disclosure relates to a vehicle seat including one or more sensors coupled to a controller for determining occupant biometrics.

SUMMARY

According to the present disclosure, an occupant support includes a vehicle seat, a sensor coupled to the vehicle seat, and a controller coupled to the sensor. The sensor provides a signal to the controller and the controller responds to the sensed signal.

In illustrative embodiments, a controller includes a sensor module, a filter module, and a biometrics module. The sensor module retrieves sensor data indicative of an occupant of a vehicle seat from one or more sensors of a vehicle. The filter module determines a filter function in a frequency range in which useful biological data may be derived. The filter function identifies one or more frequencies of noise in the sensor data and applies the filter function to the sensor data to generate filtered sensor data. The biometrics module determines biometric data associated with the occupant based on the filtered sensor data. In illustrative embodiments, the one or more sensors include a piezoelectric bend sensor, an accelerometer, or a microphone.

In illustrative embodiments, determining the filter function includes determining a notch filter at a transmission frequency of the vehicle seat while occupied by a passenger. Determining the notch filter may include determining a static resonant frequency of the vehicle seat or determining the resonant frequency based on a size of the occupant.

In illustrative embodiments, determining the size of the occupant includes receiving sensor data from one or more sensors indicative of the size of the occupant and determining the size of the occupant based on the sensor data. Determining the size of the occupant includes receiving data indicative of the size of the occupant from a second controller of the vehicle via a vehicle network.

In illustrative embodiments, determining the filter function includes determining a notch filter at a frequency based on a transmission frequency of the vehicle seat. In illustrative embodiments, determining the filter function includes receiving vehicle state data from a second controller of the vehicle via a vehicle network, and determining a notch filter at a frequency based on the vehicle state data. The vehicle state data may be indicative of engine load, engine speed, or vehicle speed.

In illustrative embodiments, determining the filter function includes characterizing the noise based on the sensor data and adapting the filter function based on the sensor data in response to characterization of the noise. In illustrative embodiments, determining the biometric data associated with the occupant includes determining a heart rate, a heart rate variability, or a respiration rate of the passenger.

In illustrative embodiments, a method includes the steps of receiving, by a controller of a vehicle, sensor data indicative of an occupant of a vehicle seat from one or more vibration sensors of the vehicle; determining, by the controller, a filter function in a biometric frequency range, wherein the filter function identifies one or more frequencies of noise in the sensor data; applying, by the controller, the filter function to the sensor data to generate filtered sensor data; and determining, by the controller, biometric data associated with the occupant based on the filtered sensor data. In illustrative embodiments, the one or more vibration sensors include a piezoelectric sensor, an accelerometer, or a microphone.

In illustrative embodiments, determining the filter function includes determining a notch filter at a resonant frequency of the vehicle seat while occupied. Determining the notch filter may include determining a transmission frequency of the vehicle seat based on a size of the occupant. In an embodiment, determining the size of the occupant includes receiving sensor data from one or more sensors indicative of the size of the occupant and determining the size of the occupant based on the sensor data. In an illustrative embodiment, determining the size of the occupant includes receiving data indicative of the size of the occupant from a second controller of the vehicle via a vehicle network.

In illustrative embodiments, determining the filter function includes determining a notch filter at a frequency based on a transmission frequency of an occupied seat. In illustrative embodiments, determining the filter function includes receiving vehicle state data from a second controller of the vehicle via a vehicle network and determining a notch filter at a frequency based on the vehicle state data. The vehicle state data may be indicative of engine load, engine speed, or vehicle speed.

In illustrative embodiments, determining the filter function includes characterizing the noise based on the sensor data and adapting the filter function based on the sensor data in response to characterizing the noise. In illustrative embodiments, determining the biometric data associated with the occupant includes determining a heart rate, a heart rate variability, or a respiration rate.

One or more computer-readable storage media in accordance with the present disclosure include a plurality of instructions that in response to being executed cause a controller to receive sensor data indicative of an occupant of a vehicle seat from one or more vibration sensors of the vehicle; determine a filter function in a biometric frequency range, wherein the filter function identifies one or more frequencies of noise in the sensor data; apply the filter function to the sensor data to generate filtered sensor data; and determine biometric data associated with the occupant based on the filtered sensor data. In illustrative embodiments, the one or more vibration sensors include a piezoelectric sensor, an accelerometer, or a microphone.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which.

Figure 1:
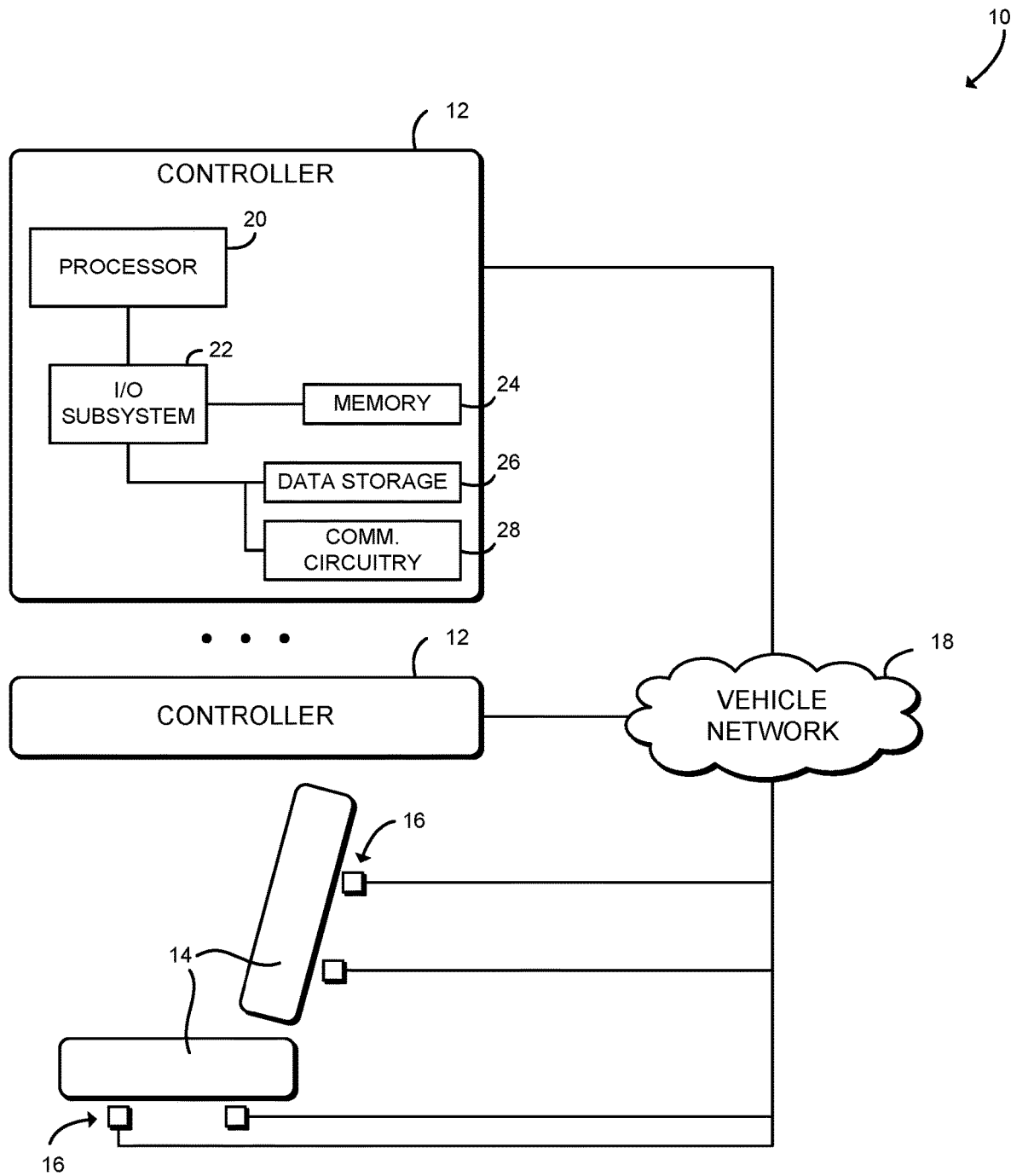
FIG. 1 is a diagrammatic view of a system in accordance with the present disclosure showing a vehicle seat, a controller, and multiple vibration sensors coupled to the controller.
Figure 2:
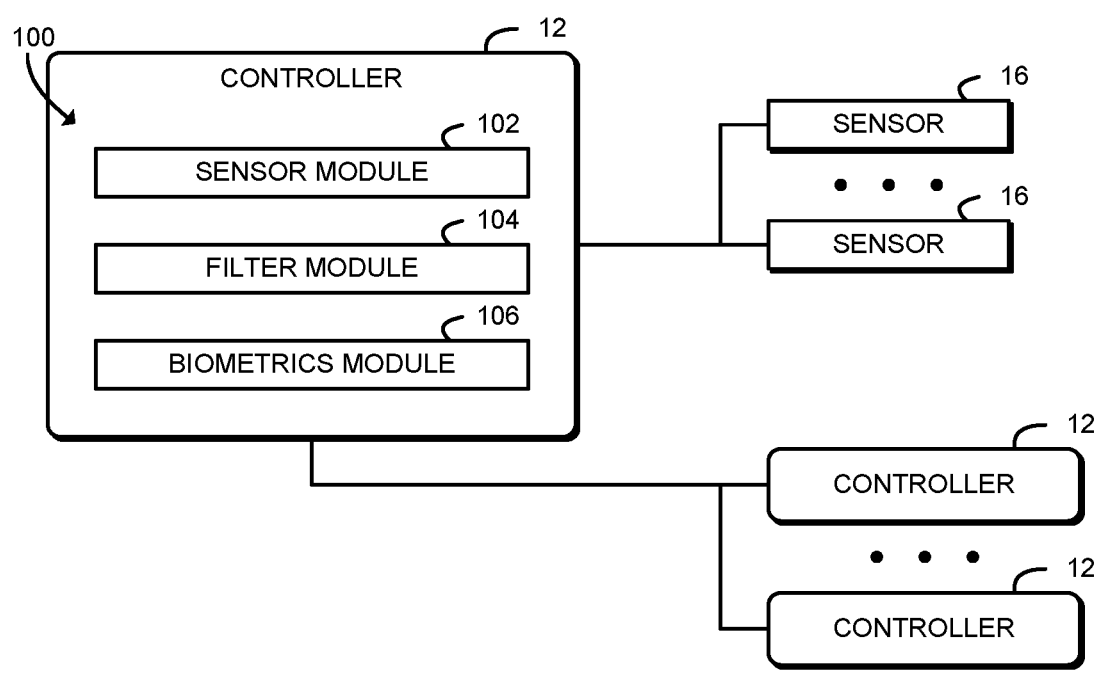
FIG. 2 is a diagrammatic view of at least one embodiment of an environment that may be established by a controller of FIG. 1.
Figure 3:
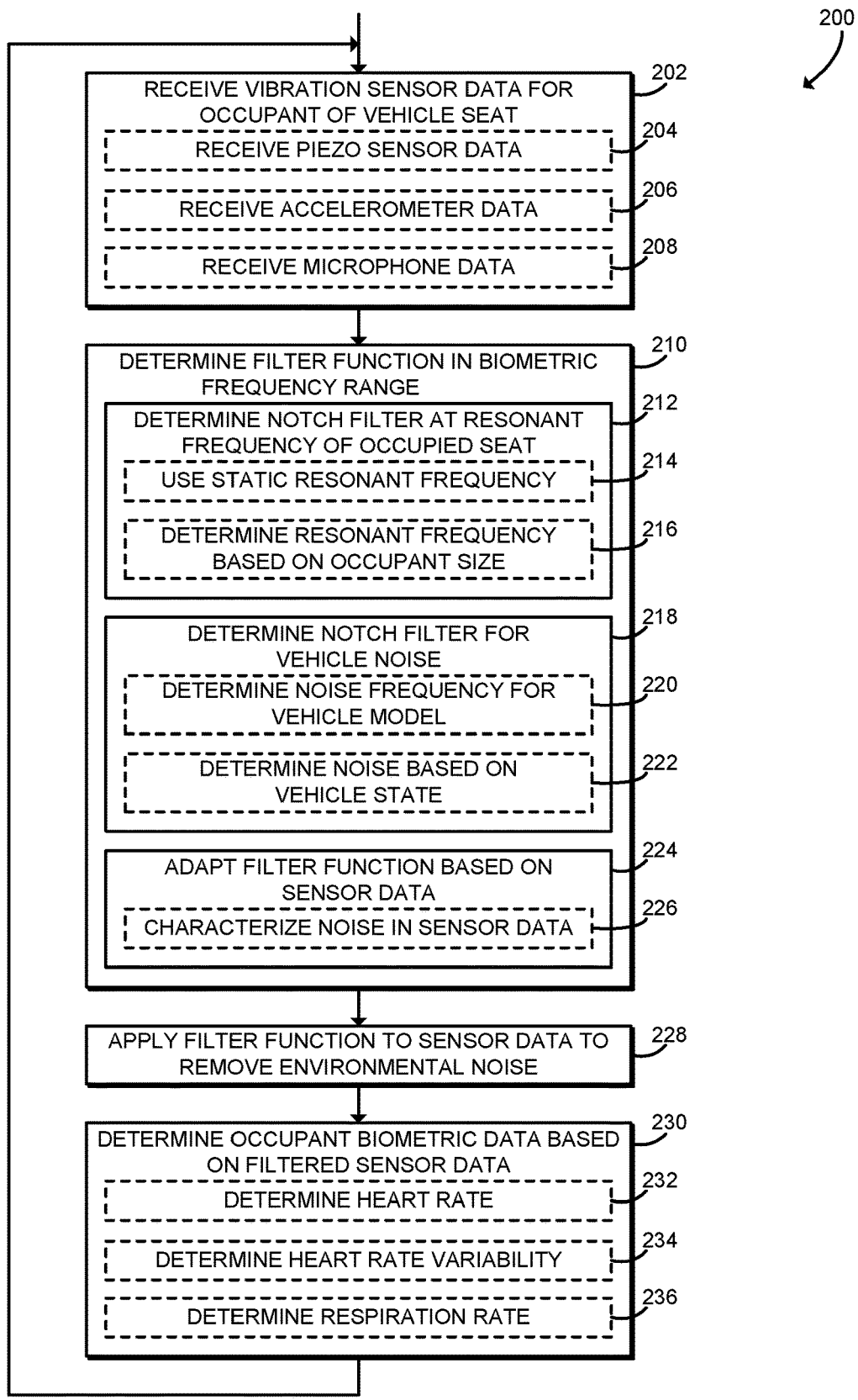
Figure 4:
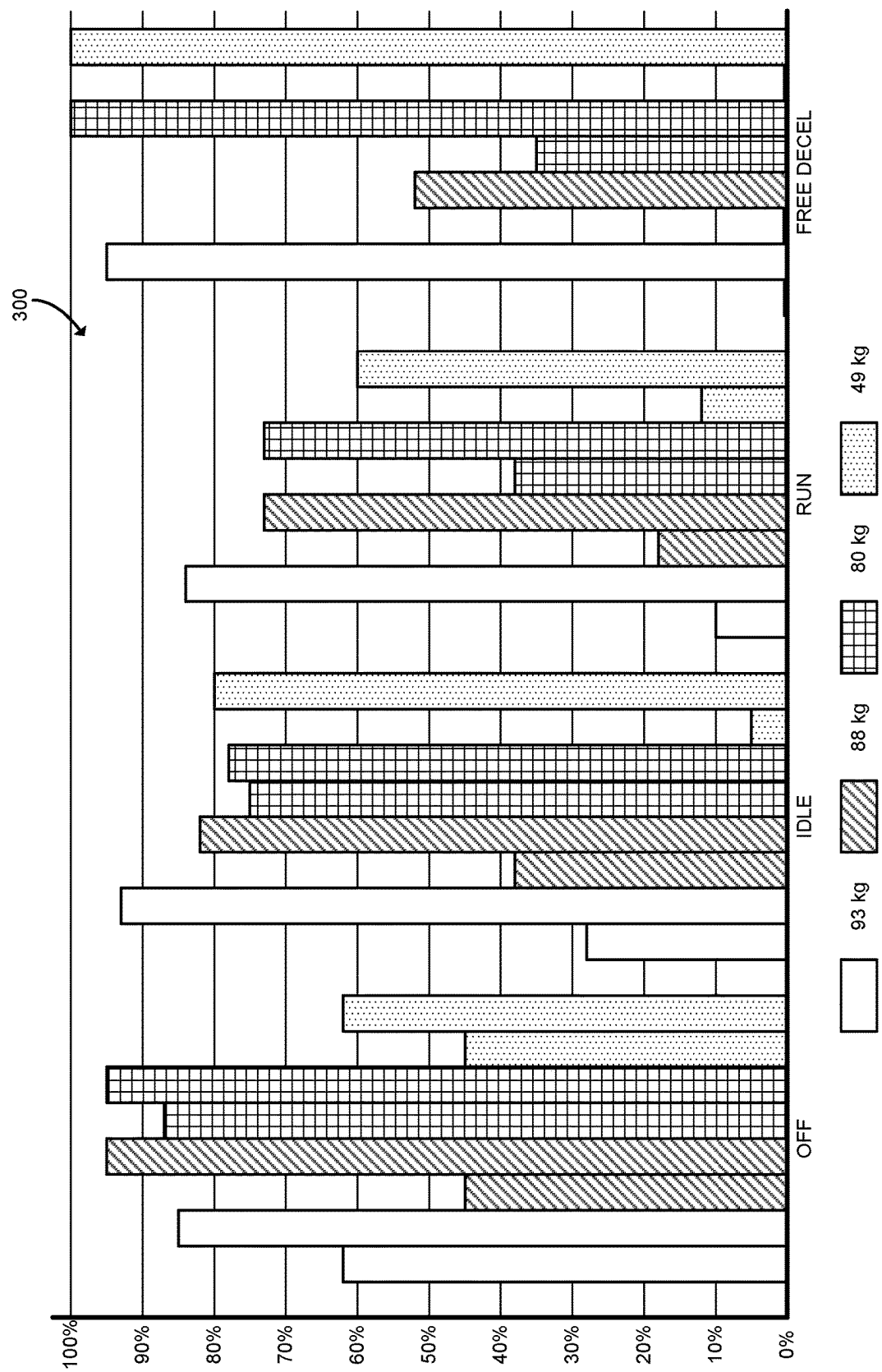

FIG. 3 is a flow diagram illustrating at least one embodiment of a method for determining occupant biometric data that may be executed by the controller of FIGS. 1 and 2; and FIG. 4 is a chart illustrating experimental results that may be achieved by the system of FIGS. 1-3 where the first bar for each occupant size in each operating state shows percent correlation to an ECG reference before the system of the present disclosure is applied and the second bar for each occupant size in each operating states shows percent correlation to the ECG reference after the system of the present disclosure is applied.

DETAILED DESCRIPTION

An embodiment of a system 10 in accordance with the present disclosure is shown in FIG. 1. The system 10 may be included in a vehicle such as a car, truck, boat, airplane, or any other suitable alternative. The illustrative system 10 includes multiple controllers 12, a vehicle seat 14, multiple vibration sensors 16, and a vehicle network 18. As described further below, in use, a controller 12 may receive sensor data from the sensors 16 and determine biometric data relating to an occupant of the vehicle seat 14 based on the sensor data.

The vehicle seat 14 may be embodied as an adjustable or otherwise movable vehicle seat and may include multiple parts, including a seat bottom, a seat back, and/or a head restraint. The vehicle seat 14 may include one or more controllers, actuators, and/or other components to provide one or more therapies. Therapies may include active surface movement including massage, lumbar and bolster, postural adjustment and other moveable surfaces that enable and/or encourage postural movement. Climate therapies may include heat, cool, venting, scent, air quality, lighting (red/blue), and music and may also be used.

As shown, the vehicle seat 14 is coupled to multiple sensors 16. Each of the sensors 16 may be embodied as any electronic device capable of measuring vibrations generated by biological processes of an occupant of the vehicle seat 14 (e.g., vibrations caused by the occupant's heartbeat, respiration, or other processes). In the illustrative embodiment, the sensors 16 are embodied as piezoelectric strips. In other embodiments, the sensors 16 may include PV piezoelectric film, piezoelectric cables, accelerometers (piezoelectric), microphones, impedance field, combinations thereof, or any other suitable vibration sensors. The sensors 16 may be included in, incorporated in, or otherwise attached to the vehicle seat 14. Thus, in some examples, the sensors 16 may be covered with vehicle seat trim and accordingly spaced apart from the occupant of the vehicle seat 14. Additionally, although illustrated as including four sensors 16, the system 10 may include a different number and/or arrangement of sensors 16.

The system 10 further includes multiple controllers 12, which each may be embodied as an electronic control unit or other controller configured to perform the functions described herein. In particular, and as described further below, a controller 12 (e.g., a controller 12 coupled to the vehicle seat 14) may be configured to receive sensor data from the sensors 16 and determine biometric data relating to the occupant of the vehicle seat 14 based on the sensor data. Thus, the system 10 may measure occupant biometrics even in a noisy environment such as the interior of a vehicle when driving. Additionally, the system 10 may measure occupant biometrics with the sensors 16 spaced apart from the occupant's body (e.g., to allow for seat trim and clothing), without requiring the sensors 16 to be attached to the occupant. By measuring the occupant biometrics, the system 10 may provide biofeedback to the occupant, trigger or suggest appropriate therapies, or perform other applications.

Each controller 12 may be embodied as any device capable of performing the functions described herein. For example, each controller 12 may be embodied as an electronic control unit, embedded controller, control circuit, microcontroller, computing device, on-board computer, and/or any other any other computing device capable of performing the functions described herein. As shown in FIG. 2, an illustrative controller 12 includes a processor 20, an I/O subsystem 22, a memory 24, a data storage device 26, and communication circuitry 28. Of course, the controller 12 may include other or additional components, such as those commonly found in an electronic control unit (e.g., various input/output devices), in other embodiments. Additionally, in some embodiments, one or more of the illustrative components may be incorporated in, or otherwise form a portion of, another component. For example, the memory 24, or portions thereof, may be incorporated in the processor 20 in some embodiments.

The processor 20 may be embodied as any type of processor capable of performing the functions described herein. For example, the processor 20 may be embodied as a microcontroller, digital signal processor, single or multi-core processor(s), or other processor or processing/controlling circuit. Similarly, the memory 24 may be embodied as any type of volatile or non-volatile memory or data storage capable of performing the functions described herein. In operation, the memory 24 may store various data and software used during operation of the processor 20 such as operating systems, applications, programs, libraries, and drivers. The memory 24 is coupled to the processor 20 via the I/O subsystem 22, which may be embodied as circuitry and/or components to facilitate input/output operations with the processor 20, the memory 24, and other components of the controller 12. For example, the I/O subsystem 22 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 22 may form a portion of a system-on-a-chip (SoC) and be incorporated, along with the processor 20, the memory 24, and other components of the controller 12, on a single integrated circuit chip.

The data storage device 26 may be embodied as any type of device or devices configured for short-term or long-term storage of data such as, for example, memory devices and circuits, memory cards, hard disk drives, solid-state drives, read-only memory, or other data storage devices. The communication circuitry 28 of the controller 12 may be embodied as any communication circuit, device, or collection thereof, capable of enabling communications between the controller 12 and other devices of the vehicle seat 14 and/or the vehicle. The communication circuitry 28 may be configured to use any one or more communication technology (e.g., wireless or wired communications) and associated protocols (e.g., Ethernet, controller area network (CAN), local interconnect network (LIN), Bluetooth®, Wi-Fi®, etc.)

to effect such communication. In some embodiments, the communication circuitry 28 may include one or more general-purpose I/O pins, analog interfaces, solid state motor control electronics, and/or other circuitry that may be used to interface with or otherwise control features of the vehicle seat 14 (e.g., seat motion, therapy, or other features).

As further shown in FIG. 1, the controllers 12 and the sensors 16 may be configured to transmit and/or receive data with each other and/or other devices over the vehicle network 18. The vehicle network 18 may be embodied as any bus, network, or other communication facility used to communicate between devices in the vehicle. For example, the vehicle network 18 may be embodied as a wired or wireless local area network (LAN), controller area network (CAN), and/or local interconnect network (LIN). Thus, the vehicle controllers 12 may include one or more additional electronic control units, embedded controllers, engine computers, or other computing devices used to control various vehicle functions. In particular, the controller 12 may be configured to communicate with one or more additional vehicle controllers 12 via the vehicle network 18 to determine the state of the vehicle, for example to determine whether the ignition is on, to determine engine speed or engine load, to determine vehicle speed, or to determine other vehicle state. Additionally or alternatively, although shown as communicating directly with the vehicle network 18, it should be understood that in some embodiments the sensors 16 may be coupled directly to one or more controllers 12 (e.g., a seat controller 12) without using the vehicle network 18.

Referring now to FIG. 2, in the illustrative embodiment, a controller 12 establishes an environment 100 during operation. The illustrative environment 100 includes a sensor module 102, a filter module 104, and a biometrics module 106. The various modules of the environment 100 may be embodied as hardware, firmware, software, or a combination thereof. For example the various modules, logic, and other components of the environment 100 may form a portion of, or otherwise be established by, the processor 20 or other hardware components of the controller 12. As such, in some embodiments, any one or more of the modules of the environment 100 may be embodied as a circuit or collection of electrical devices (e.g., sensor circuitry, filter circuitry, biometrics circuitry, etc.).

The sensor module 102 is configured to receive sensor data indicative of an occupant of the vehicle seat 14 from one or more vibration sensors 16 of the vehicle. As described above, the sensors 16 may include, for example, a piezoelectric sensor, an accelerometer, or a microphone.

The filter module 104 is configured to determine a filter function in a biometric frequency range. The filter function identifies one or more frequencies of noise in the sensor data. For example, the filter function may include a notch filter at a resonant frequency of the vehicle seat 14 while occupied or at a transmission frequency of the vehicle. As another example, the filter function may include a notch filter at a frequency determined based on vehicle state data received from another controller 12 of the vehicle. The filter module 104 is further configured to apply the filter function to the sensor data to generate filtered sensor data.

The biometrics module 106 is configured to determine biometric data associated with the occupant of the vehicle seat 14 based on the filtered sensor data. For example, the biometrics module 106 may be configured to determine a heart rate, a heart rate variability, or a respiration rate.

Referring now to FIG. 3, in use, the controller 12 may execute a method 200 for determining biometric data of an occupant of the vehicle seat 14. In some examples, the operations of the method 200 may be performed by one or more modules of the environment 100 of the controller 12 as shown in FIG. 2. The method 200 begins in block 202, in which the controller 12 receives vibration sensor data from one or more sensors 16. The vibration sensor data is indicative of vibrations caused by an occupant of the vehicle seat 14. In some examples, in block 204 the controller 12 may receive sensor data from one or more piezoelectric sensors 16. In some examples, in block 206 the controller 12 may receive sensor data from one or more accelerometers 16. In some embodiments, in block 208 the controller 12 may receive sensor data from one or more microphones 16.

In block 210, the controller 12 determines a filter function in a biometric frequency range. The biometric frequency range includes frequencies that may be used to determine biometric data of the occupant such as heart rate or respiration. The filter function may filter out one or more frequencies within the biometric frequency range that carry environmental noise, vehicle noise, are saturated, or otherwise interfere with biometric signals. For example, an impact, such as a pot hole, drives all frequencies. The suspension of the vehicle mutes the impact, reducing the amplitude and generating transmission frequency of the vehicle and drive dynamics (e.g., comfort or sports mode) sweeping and general noisy vibration will drive multiple frequencies. Engine vibrations are higher than this range, but similar to an impact tend to excite all frequencies in vibration. High energy engine vibrations may excite sub-harmonics in the range of transmission frequency of the vehicle seat.

In block 212, the controller 12 may determine a notch filter (i.e., a narrow band-reject filter) at a resonant frequency of the vehicle seat 14 while occupied. A vehicle seat 14, like a tuning fork, may resonate when subjected to its natural frequency. Modal analysis determines the natural frequency response of a structure to an impact or excitation. When the vehicle seat 14 is subjected to vibrations from the vehicle at the seat's natural frequency, the vehicle seat 14 may respond, resonate, and transmit its natural frequencies. The transmissibility of the vehicle seat 14 while occupied is affected by the natural frequency of the vehicle seat 14, as discussed above, as well as the addition of the occupant. The occupant adds mass, which tends to lower the frequency, adds structure which tends to raise the frequency, and adds damping, which generally reduces amplitude and broadens the band and/or bands of affected frequencies. The size, position, posture, and/or movement of the occupant may add further variation.

In some embodiments, in block 214 the controller 12 may use a predetermined or otherwise static frequency for the notch filter at the resonant frequency of the occupied vehicle seat 14. As described above, occupying the vehicle seat 14 may mute, lower, and/or broaden the frequency response of the unloaded vehicle seat 14. The change in frequency response may depend on the size of the occupant (e.g., the weight, height, or other size metric of the occupant). In some embodiments, a predetermined frequency may be selected to treat the whole population of potential occupants equally by using percent improvement, which is the best filter percent performance minus no filter percent performance. In that embodiment, the most improvement would apply to the worst case and thus would emphasize outliers. Accordingly, this would result in the entire population achieving about the same result. Additionally or alternatively, in some embodiments a predetermined frequency may be selected based on a body type normal distribution. In that embodiment, the filter may be statistically weighted by body size, and the resulting filter function would be biased toward the 50th percentile body size.

In some embodiments, in block 216 the controller 12 may determine the resonant frequency based on the size of the occupant (e.g., the occupant's height, weight, and/or other size metric). The controller 12 may adjust a base filter function based on the size of the occupant (e.g., muting, lowering, and/or broadening the frequency response as described above). For example, in some embodiments, the controller 12 may determine the size of the occupant based on user anthropometric information or other user profile information. The controller 12 may receive the anthropometric information, for example, from another controller 12 over the vehicle network 18 or via an input from the occupant. Additionally or alternatively, the controller 12 may determine the size of the user based on sensor data received from the sensors 16 and/or additional sensors of the vehicle. For example, the controller 12 may determine the weight of the user based on sensor data received from one or more load cells, strain gauges, or other weight sensors.

In some embodiments, in block 218 the controller 12 may determine a notch filter for one or more frequencies of noise generated and/or transmitted by the vehicle. A vehicle is typically a noisy environment with multiple potential sources of vibration other than the sources of biometric data from an occupant. For example, vibration may come from the vehicle drivetrain (e.g., the engine transmission and the exhaust) and the road (e.g., suspension and vehicle dynamics.) Noise may also be produced by the vehicle acoustic environment (e.g., music and HVAC) and/or vehicle seat 14 features (e.g., adjustment, massage, vent, or other features). Actions of the occupant, such as speaking, movement, and/or posture may also affect vibration sensor readings.

In some embodiments, in block 220 the controller 12 may determine the noise frequencies based on the model of the vehicle. Every vehicle model may have a particular transmission frequency. In some embodiments, in block 222 the controller 12 may determine the frequency of noise based on vehicle state. The controller 12 may receive the vehicle state data or other vehicle information from one or more other controllers 12 of the vehicle, such as an engine controller 12. The vehicle state may indicate whether the vehicle is on or off, the speed of the engine (i.e., RPM), the engine load, the throttle position, the speed of the vehicle, or other attributes of the driving state of the vehicle. When characterized and associated with the transmission frequency of the vehicle model, the vehicle state information may be used to adopt an appropriate filter function. The engine may provide periodic excitation which the vehicle seat will transmit at the transmission frequency determined by the seat structure and the occupant size. This has been observed during idle and when the vehicle is freely decelerating. Thus, a notch filter may be used when the engine load indicates free deceleration, which may be determined as a function of engine RPM and vehicle speed.

In block 224, the controller 12 may adapt the filter function based on sensor data received from the sensors 16. In some embodiments, in block 226 the controller 12 may characterize the noise in sensor data received from the sensors 16. This can be derived from the transients of the sensors 16 themselves and/or other sensors. In some embodiments, the controller 12 may use a learning system that senses and characterizes noise. By sensing occupant size, weight, posture, and motion under different vehicle conditions (e.g., vehicle off, vehicle on, driving, pot hole impact, etc.), the controller 12 may characterize, learn, and adapt an appropriate filter regimen.

After determining the filter function, in block 228, the controller 12 applies the filter function to the sensor data to generate filtered sensor data. Thus, the controller 12 may remove environmental noise from the filtered sensor data.

In block 230, the controller 12 determines biometric data associated with the occupant based on the filtered sensor data. In particular, the controller 12 may analyze sensor data in the biometric frequency range. In some embodiments, in block 232 the controller 12 may determine the heart rate of the occupant. In some embodiments, in block 234 the controller 12 may determine heart rate variability of the occupant. The heart rate variability may be associated with alertness and stress level of the occupant. In block 236, the controller 12 may determine the respiration rate of the occupant. After determining the biometric data, the method 200 loops back to block 202 to continue processing sensor data. The controller 12 may use the biometric data for biofeedback, to initiate therapy, or for other uses. Additionally or alternatively, although illustrated as executing sequentially, it should be understood that the operations of the method 200 may be performed in a different order and/or at different times. For example, in some embodiments, the filter function may be determined ahead of time prior to receiving the sensor data.

Referring now to FIG. 4, chart 300 illustrates experimental results that may be achieved by the system 10. The chart 300 illustrates the percent correlation to reference biometric data that is achieved by the system 10 as compared to the percent correlation achieved based on unfiltered sensor data. In the illustrative experimental results, the biometric data is occupant heart rate, and the reference data was generated directly using an electrocardiograph (ECG) harness. As shown, for a 93-kilogram occupant, the system 10 improves from about 62% to about 85% in the vehicle off state, from about 28% to about 93% in the idle state, from about 10% to about 84% in the run state, and from about 0% to about 95% in the free deceleration state. For an 88-kilogram occupant, the system 10 improves from about 45% to about 95% in the vehicle off state, from about 38% to about 82% in the idle state, from about 18% to about 73% in the run state, and from about 0% to about 52% in the free deceleration state. For an 80-kilogram occupant, the system 10 improves from about 87% to about 95% in the vehicle off state, from about 75% to about 78% in the idle state, from about 38% to about 73% in the run state, and from about 35% to about 100% in the free deceleration state. For a 49-kilogram occupant, the system 10 improves from about 45% to about 62% in the vehicle off state, from about 5% to about 80% in the idle state, from about 12% to about 60% in the run state, and from about 0% to about 100% in the free deceleration state.

The invention claimed is:

1. A controller for biometric measurement, the controller comprising
   a sensor module to receive sensor data indicative of vibrations generated by a biological process of an occupant of a vehicle seat from one or more vibration sensors of a vehicle,
   a filter module to (i) determine a filter function in a biometric frequency range, wherein the filter function identifies one or more frequencies of noise in the sensor data, wherein to determine the filter function comprises to determine a notch filter at a transmission frequency of the vehicle seat while occupied, wherein the notch filter is a narrow band-reject filter and (ii) apply the filter function to the sensor data to generate filtered sensor data, and a biometrics module to determine biometric data associated with the biological process of the occupant based on the filtered sensor data.

2. The controller of claim 1, wherein to determine the notch filter comprises to determine a static vibrational resonant frequency of the vehicle seat.

3. The controller of claim 1, wherein to determine the notch filter comprises to determine, based on a size of the occupant, a vibrational resonant frequency of the vehicle seat.

4. The controller of claim 3, wherein to determine the size of the occupant comprises to
receive sensor data from one or more sensors indicative of the size of the occupant and
determine the size of the occupant based on the sensor data.

5. The controller of claim 3, wherein to determine the size of the occupant comprises to receive data indicative of the size of the occupant from a second controller of the vehicle via a vehicle network.

6. The controller of claim 1, wherein to determine the filter function comprises to
receive vehicle state data from a second controller of the vehicle via a vehicle network and
determine the notch filter based on the vehicle state data.

7. The controller of claim 6, wherein the vehicle state data is indicative of engine load, engine speed, or vehicle speed.

8. The controller of claim 1, wherein to determine the filter function comprises to
characterize the noise based on the sensor data and
adapt the filter function based on the sensor data in response to characterization of the noise.

9. A method for biometric measurement, the method comprising the steps of:
receiving, by a controller of a vehicle, sensor data indicative of an occupant of a vehicle seat from one or more vibration sensors of the vehicle,
determining, by the controller, a filter function in a biometric frequency range, wherein the filter function identifies one or more frequencies of noise in the sensor data, wherein determining the filter function comprises determining a notch filter at a resonant frequency of the vehicle seat while occupied applying, by the controller, the filter function to the sensor data to generate filtered sensor data, and
determining, by the controller, biometric data associated with the occupant based on the filtered sensor data.

10. The method of claim 9, wherein determining the notch filter comprises determining a static resonant frequency of the vehicle seat.

11. The method of claim 9, wherein determining the notch filter comprises determining, based on a size of the occupant, the resonant frequency.

12. The method of claim 9, wherein determining the filter function comprises
receiving vehicle state data from a second controller of the vehicle via a vehicle network and
determining the notch filter based on the vehicle state data.

13. One or more non-transitory computer-readable storage media comprising a plurality of instructions that in response to being executed cause a controller to:
receive sensor data indicative of an occupant of a vehicle seat from one or more vibration sensors of the vehicle,
determine a filter function in a biometric frequency range, wherein the filter function identifies one or more frequencies of noise in the sensor data, wherein to determine the filter function comprises to determine a notch filter at a resonant frequency of the vehicle seat while occupied,
apply the filter function to the sensor data to generate filtered sensor data, and
determine biometric data associated with the occupant based on the filtered sensor data.

14. The one or more non-transitory computer-readable storage media of claim 13, wherein to determine the notch filter comprises to determine a static resonant frequency of the vehicle seat.

15. The one or more non-transitory computer-readable storage media of claim 13, wherein to determine the notch filter comprises to determine, based on a size of the occupant, the resonant frequency.

16. The one or more non-transitory computer-readable storage media of claim 13, wherein to determine the filter function comprises to receive vehicle state data from a second controller of the vehicle via a vehicle network and determine the notch filter based on the vehicle state data.

* * * * *